(12) United States Patent
Nackaerts

(10) Patent No.: US 10,747,851 B2
(45) Date of Patent: Aug. 18, 2020

(54) SEGMENTED PLATFORM FOR ITEMS

(71) Applicant: NXP B.V., Eindhoven (NL)

(72) Inventor: Axel Nackaerts, Haasrode (BE)

(73) Assignee: NXP B.V., Eindhoven (NL)

( * ) Notice: Subject to any disclaimer, the term of this patent is extended or adjusted under 35 U.S.C. 154(b) by 239 days.

(21) Appl. No.: 15/619,104

(22) Filed: Jun. 9, 2017

(65) Prior Publication Data

US 2018/0357388 A1    Dec. 13, 2018

(51) Int. Cl.
   *G05B 23/02*    (2006.01)
   *G06F 19/00*    (2018.01)
   *G06Q 10/08*    (2012.01)
   *G06Q 50/12*    (2012.01)

(52) U.S. Cl.
   CPC ......... *G06F 19/3462* (2013.01); *G06Q 10/08* (2013.01); *G06Q 50/12* (2013.01)

(58) Field of Classification Search
   CPC ..... G06F 19/3462; G06Q 10/08; G06Q 50/12
   USPC .......................................................... 340/3.7
   See application file for complete search history.

(56) References Cited

U.S. PATENT DOCUMENTS

| | | | |
|---|---|---|---|
| 5,954,641 A * | 9/1999 | Kehr .................... | A61B 5/0002 600/300 |
| 6,411,567 B1 | 6/2002 | Niemiec et al. | |
| 6,973,371 B1 | 12/2005 | Benouali | |
| 7,126,879 B2 | 10/2006 | Snyder | |
| 7,336,564 B2 | 2/2008 | Feodoroff | |
| 7,946,101 B1 | 5/2011 | McGonagle et al. | |
| 9,101,530 B2 | 8/2015 | Wilson et al. | |
| 2008/0059228 A1 | 3/2008 | Bossi et al. | |
| 2010/0031611 A1 * | 2/2010 | Ali ....................... | G06F 19/3462 53/467 |
| 2011/0288380 A1 * | 11/2011 | Inciardi ................. | G01M 3/165 600/301 |
| 2012/0203573 A1 * | 8/2012 | Mayer .................. | G06F 19/3456 705/3 |
| 2014/0156296 A1 * | 6/2014 | Stenzler .............. | G06F 19/3456 705/2 |
| 2016/0120758 A1 * | 5/2016 | Pi .............................. | A61J 1/03 340/870.07 |
| 2017/0300659 A1 * | 10/2017 | Ziv ........................ | G06F 19/326 |
| 2018/0082244 A1 * | 3/2018 | Brazeau ................ | G06F 3/0304 |
| 2018/0170618 A1 * | 6/2018 | Tunesi ..................... | G08B 5/36 |

FOREIGN PATENT DOCUMENTS

CN         101802830 A    8/2010

OTHER PUBLICATIONS

Rise Acero; Home Page from Website; retrieved from the internet https://www.acreo.se/expertise/printed-and-organic-electronics; 43 pages (Jun. 8, 2017).

* cited by examiner

*Primary Examiner* — Naomi J Small

(57) ABSTRACT

One example discloses a segmented platform, including: a set of cells configured to receive a set of different items; a cell content circuit configured to map each different item to at least one of the cells; a set of visual indicators coupled to the set of cells; and a cell selector circuit configured to identify a selected item from the set of different items and activate a visual indicator from the set of visual indicators corresponding to a selected cell from the set of cells that is configured to contain the selected item.

18 Claims, 8 Drawing Sheets

SEGMENTED PLATFORM FOR ITEMS

The present specification relates to systems, methods, apparatuses, devices, articles of manufacture and instructions for item management.

SUMMARY

According to an example embodiment, a segmented platform, comprising: a set of cells configured to receive a set of different items; a cell content circuit configured to map each different item to at least one of the cells; a set of visual indicators coupled to the set of cells; and a cell selector circuit configured to identify a selected item from the set of different items and activate a visual indicator from the set of visual indicators corresponding to a selected cell from the set of cells that is configured to contain the selected item.

In another example embodiment, the set of cells are configured to receive a blister package.

In another example embodiment, the set of cells are configured to be optically projected over a structure containing the set of different items.

In another example embodiment, the set of different items differ by at least one of: a medicine dosage level, a quality level, an order of completion, an order of assembly, an order of repair, an order of food preparation, or a recipe.

In another example embodiment, the set of different items include at least one of: a pill, a medicine, a disposable device, a repair kit item, an assembly kit item, a teaching kit item, a test kit item, a food, a nutrition level, an ingredient, or a chemical.

In another example embodiment, further comprising: a set of detectors configured to detect a presence of the different items in the set of cells.

In another example embodiment, further comprising: a cell status circuit coupled to the set of detectors and configured to, generate a presence signal for the selected cell if the selected item is still present in the selected cell; and generate an absent signal for the selected cell if the selected item is no longer present in the selected cell.

In another example embodiment, the cell selector circuit is configured to identify a next selected item from the set of different items in response to the cell status circuit changing the presence signal to the absent signal for the selected cell.

In another example embodiment, multiple cells within the set of cells are configured to receive just one of the different items.

In another example embodiment, the visual indicators include at least one of: a single visual indicator coupled to a single cell; a single visual indicator coupled to a set of cells; or a visual indicator pattern coupled to a set of cells.

In another example embodiment, the visual indicators pictorially represent at least one of: a user quality score, a color based status indicator, a countdown timer, an item expiration date, an item superseded indicator, or a do not use indicator.

In another example embodiment, the visual indicators pictorially represent a first color indicating an item to remove now, a second color indicating an item to remove soon, and a third color indicating an item not to remove.

In another example embodiment, the cell selector circuit is configured to identify the selected item from the set of different items based on at least one of: a medicine dosage level, a quality level, an order of completion, an order of assembly, an order of repair, an order of food preparation, a recipe, a chemical, or a type of material.

In another example embodiment, further comprising a user input sensor configured to collect a set of user specific attributes; and wherein the cell selector circuit is configured to identify the selected item from the set of different items based on the set of user specific attributes received from the user input sensor.

In another example embodiment, the user specific attributes include at least one of: a user biomarker, blood pressure, glucose level, hormone level, virus or bacterial level, a problem identification level, a device upgrade level, a device repair level, or a professional skill level.

In another example embodiment, the user input sensor is configured to be embedded in a structure containing the set of different items, and to be in communication with the segmented platform.

In another example embodiment, the cell selector circuit is further configured to identify the selected item from the set of different items based on a dynamic prescription received from a doctor.

According to an example embodiment, a method for selecting cells within a segmented package, comprising: receiving a set of different items within a set of cells; mapping each different item to at least one of the cells; identifying a selected item from the set of different items; and activating a visual indicator from a set of visual indicators corresponding to a selected cell from the set of cells that is configured to contain the selected item.

In another example embodiment, further comprising: collecting a set of user specific attributes from a user input sensor; and identifying the selected item from the set of different items based on the set of user specific attributes.

In another example embodiment, further comprising: generating a presence signal for the selected cell if the selected item is still present in the selected cell; generating an absent signal for the selected cell if the selected item is no longer present in the selected cell; and identifying a next selected item from the set of different items in response to a changing of the presence signal to the absent signal for the selected cell.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

Figure 1:
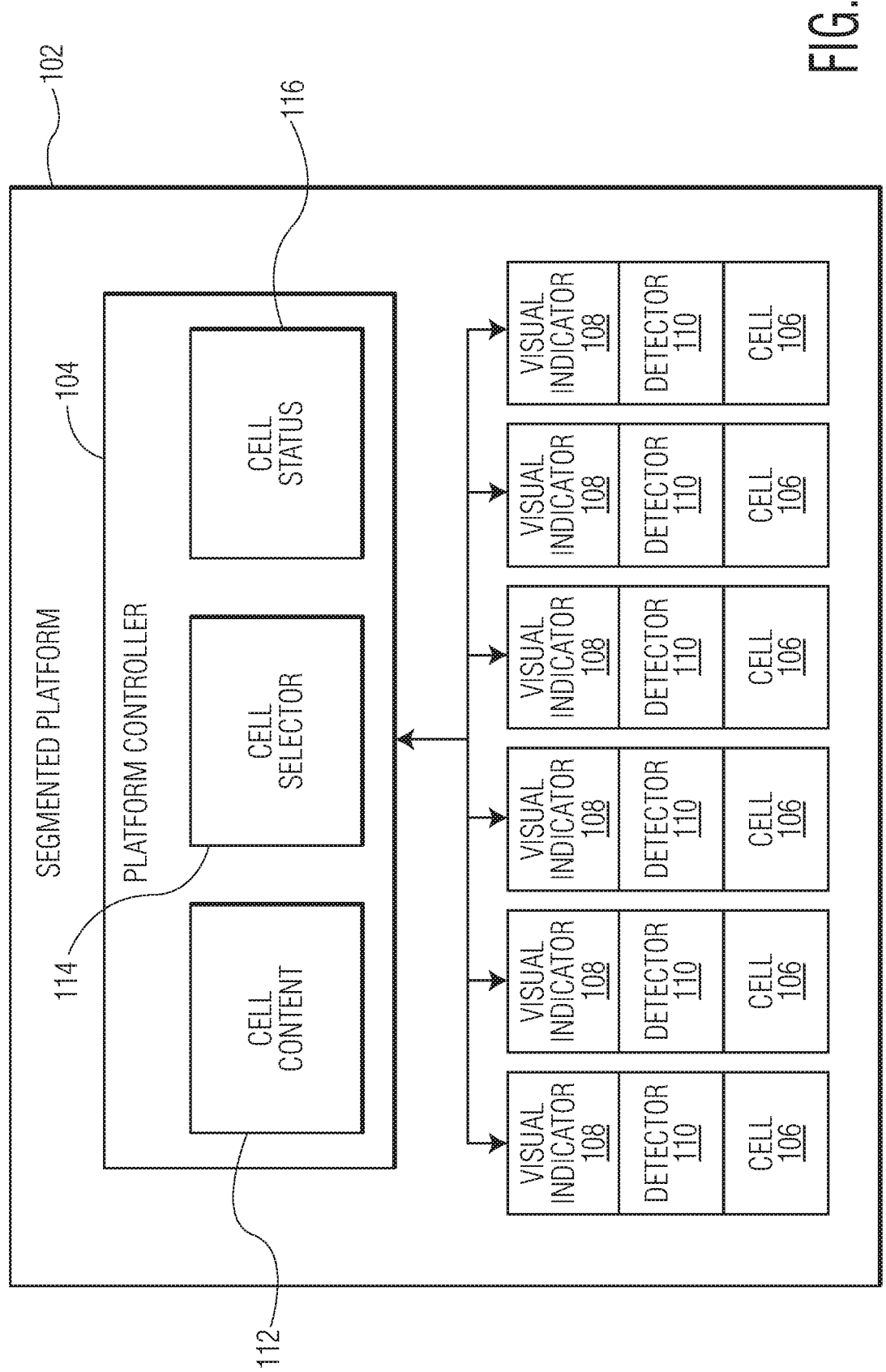
FIG. 1 is a first example of a segmented platform.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Organized items in areas such as medicine, teaching, assembly, repair, and so on is important for the proper construction, operations and wellbeing of objects and people. Such organization in a medical environment could be critical toward performing an operation or taking one's medicine.

Structures, systems and methods for facilitating such efforts support positive outcomes in the many domains where organization and disciplined routine is important, including: medical, aeronautics, mechanical, military, automotive, manufacturing, maintenance, repair, emergency response, teaching, food preparation, recipes (chemical, food, etc.), and fabrication.

While various example embodiments now to be discussed herein relate mainly to pill and/or medicine dispensing, the structures and techniques discussed herein apply to various other organized and/or dispensed items.

FIG. 1 is a first example of a segmented platform 102. The segmented platform 102 includes a platform controller 104 coupled to a set of cells 106 (e.g. cavities), a set of visual indicators 108, and a set of detectors 110. The platform controller 104 includes a cell content circuit 112, a cell selector circuit 114, and a cell status circuit 116. The set of cells 106 (e.g. cavities) are configured to receive a set of items (not shown), which in some example embodiments are a set of different items. Segmented is herein defined to at least refer to the set of cells 106.

Different items are herein defined to include items that differ in at least one of the following ways: shape, function, content, order of use, and so on.

In some example embodiments, the set of cells 106 are configured to receive a set of different items. The cell content circuit 112 is configured to map each of these different items to at least one of the cells 106. The set of visual indicators 108 are coupled to the set of cells 106. The cell selector circuit 114 is configured to identify a selected item from the set of different items and activate a visual indicator from the set of visual indicators 108 corresponding to a selected cell from the set of cells 106 that is configured to contain the selected item.

The set of cells 106 can either be fixed in a structure (e.g. a structure configured to receive a disposable blister package), perhaps optically projected over a table surface or another structure (e.g. a repair kit package, box, etc.) containing the set of different items, coupled magnetically or with adhesive to specific positions on a surface, and so on. In some example embodiments, multiple cells within the set of cells 106 are configured to receive just one of the different items (e.g. perhaps a particularly large item).

The set of different items in some example embodiments can differ by at least one of: a medicine dosage level, a quality level, an order of completion, an order of assembly, an order of repair, an order of mixing, and an order of food preparation. The set of different items can specifically include at least one of: a pill, a medicine, a disposable device, a repair kit item, an assembly kit item, a teaching kit item, a test kit item, a chemical, and a food item.

The set of detectors 110 are configured to detect a presence of the different items in the set of cells 106 and thus can sense which items have been removed. Depending upon how the set of cells 106 are created, the set of detectors 110 may also vary (e.g. wire fracture, optical sensing, magnetic sensing, ultrasonic sensing, capacitive sensing, etc.).

The cell status circuit 116 is coupled to the set of detectors 110 and configured to, generate a presence signal for the selected cell if the selected item is still present in the selected cell; and generate an absent signal for the selected cell if the selected item is no longer present in the selected cell.

The cell selector circuit 114 is configured to identify a next selected item from the set of different items in response to the cell status circuit 116 changing the presence signal to the absent signal for the selected cell. For example, the cell selector circuit 114 can be configured to identify the selected item based on at least one of: a medicine dosage level, a quality level, an order of completion, an order of assembly, an order of repair, a order of food preparation, and following a recipe (chemical, food, etc.).

The set of visual indicators 108 can be used to facilitate a user in identifying which item to select. The visual indicators 108 in various embodiments can include at least one of: a single visual indicator coupled to a single cell; a single visual indicator coupled to a set of cells 106; a visual indicator pattern coupled to a set of cells 106, or multiple visual indicators coupled to one or more cells 106.

The visual indicators 108 can in various example embodiments pictorially represent at least one of: a user quality score, a color based status indicator, a countdown timer, an item expiration date, an item superseded indicator, or a do not use indicator.

For example the visual indicators 108 can be used to pictorially represent a first color indicating an item to remove now, a second color indicating an item to remove soon, and a third color indicating an item not to remove.

Particular visual indicator 108 colors would depend upon their application and can include: a projected spotlight that highlights a particular cell, variable color and/or segmentations (e.g. partial circle segments) that encircles or is next to the exact pill to be taken, a visual count down timer, as time gets nearer to take pill such as yellow meaning take pill soon and green meaning take pill now, and red meaning don't take this pill/medicine since perhaps the dosage is wrong or the pill/medicine has expired.

Thus the segmented platform's 102 visual indicators 108 and disparate item content not only combats user forgetfulness or lack of knowledge, but also can provide dosage and other flexibilities.

Figure 2:
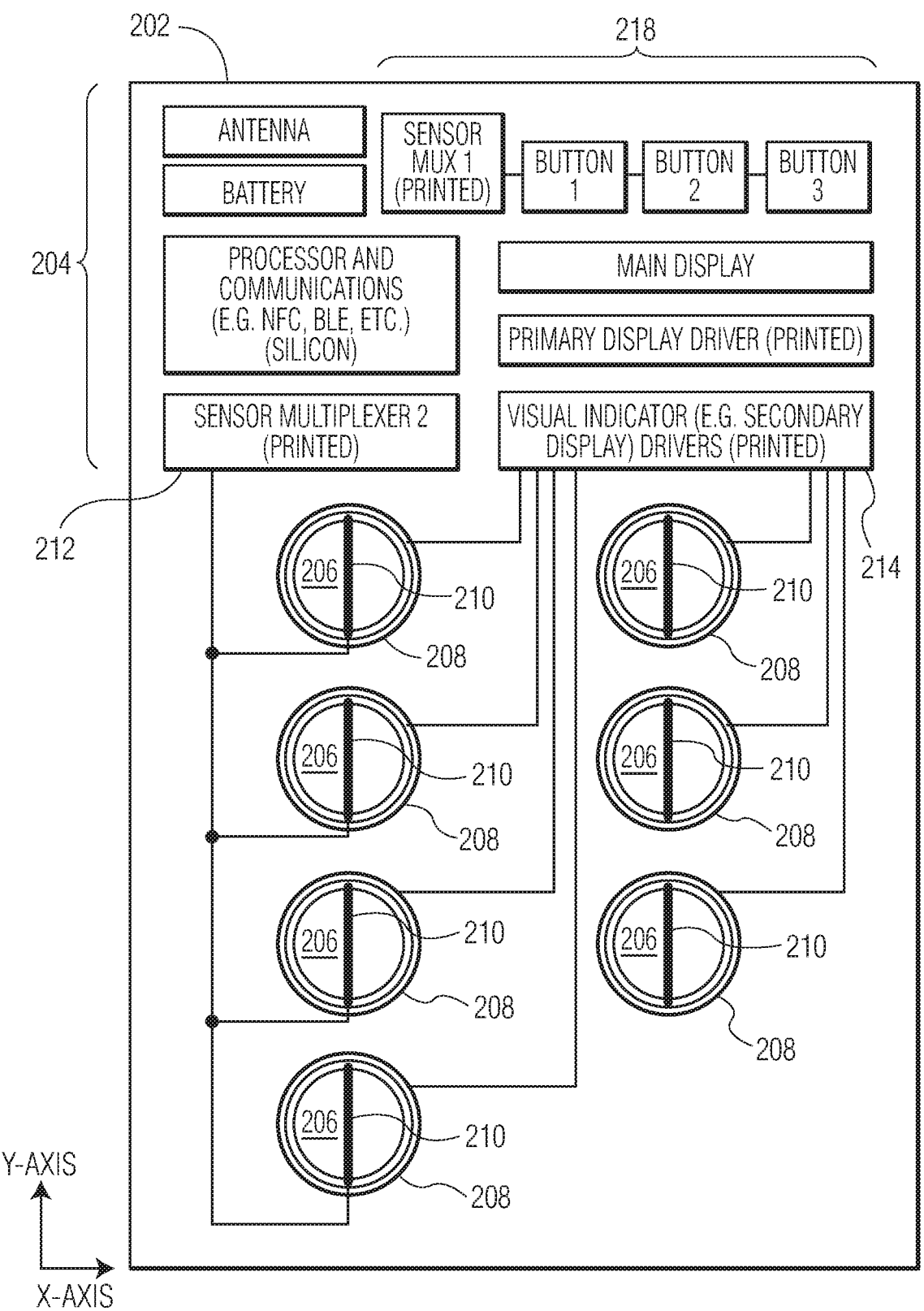
FIG. 2 is a second example of the segmented platform.

FIG. 2 is a second example 202 of the segmented platform 102. The segmented platform 202 includes a platform controller 204, a set of cells 206 configured to distinguish a set of different items (not shown), a set of visual indicators 208, a set of detectors 210, and a user interface 218. Additional elements (e.g. antenna, battery, etc.) shown in FIG. 2, but not herein specifically identified can in various embodiments also be included.

The platform controller 204 includes a cell content circuit 212 (e.g. a processor fabricated in a silicon chip and a sensor multiplexer 2 fabricated by printing on a substrate), a cell selector circuit 214 (e.g. a processor fabricated in a silicon chip and a secondary display driver fabricated by printing on a substrate), a cell status circuit (e.g. a processor fabricated in a silicon chip, and a sensor multiplexer 2 fabricated by printing on a substrate).

Thus the segmented platform's 202 components are in some example embodiments either fabricated as a silicon chip or printed on a substrate. Engineering decisions on what to print and what to chip in such a hybrid blister package can be based on cost, energy, and disposability concerns. Some examples of the segmented platform 102 are built with both monolithically integrated components (e.g. silicon integrated circuits) and printed components. Human interaction can be via buttons (e.g. membrane switches) and display.

The segmented platform 102 can consist of multiple parts, assembled on a substrate that can be flexible. The substrate in some examples integrates passive components and active components. The components can be either discrete (resistors, capacitors, integrated circuits), or printed (lines of conductive polymers, metal powders, organic or inorganic thin film transistors, display elements).

The segmented platform 102 can include both mass-produced complex elements (e.g. silicon integrated circuits (IC)) and printed electronic elements that are unique to each application of the segmented platform 102. Silicon in some embodiments is cheap to produce, can handle complex tasks, but is difficult and expensive to customize. Some printed circuits cannot handle complex tasks fast enough or securely enough, or complex circuits (e.g. non-volatile memory, security and authentication), but are easy to customize. However, since example embodiments of the segmented platform 102 combines the strengths of both silicon and printing technologies, a powerful yet customizable solution may be obtained.

The segmented platform's 202 in this example embodiment is a fold and stick credit-card-like fabrication. Alternate embodiments could be housed in a rigid box.

In some example embodiments, the main display shown in FIG. 2 displays a user quality score and the better or more accurately the user takes the pills, the higher the score. This form of gamification can lead to improved patient behavior.

In this example, the segmented platform 202 is configured to receive a blister package (e.g. see 408 in FIG. 4B) containing seven pills. Also shown are: a battery, an NFC (Near Field Communications), BLE (Bluetooth Low Energy) communications circuit combined with other processing elements, an antenna, and three buttons for user interaction. In some example embodiments, distributed throughout the segmented platform 202 are also: microcontrollers, a power management unit, a radio, a temperature sensor, a real-time clock, memories, and input/output connections. The segmented platform 202 printed electronic circuits in this embodiment include two input multiplexers and two display drivers.

One example use case is as follows: a manufacture fabricates and initializes the segmented platform 202; after filling with pills, the platform controller 204 starts monitoring environmental information (e.g. temperature, humidity, shock); at a pharmacy, content and quality of the items are checked (NFC communication, download temperature logging information); at delivery to customer, a doctor's prescription is downloaded into the segmented platform 202 (e.g. smart blister) using the NFC connection; the blister then starts monitoring temperature and pill removal; at the user's home, the smart blister will indicate which pill and at what time the pills should be taken (e.g. "Next pill at 5 p.m."); one hour before due time, the blister will indicate which pill to take using the secondary display; the blister will monitor whether the correct pill is taken and indicate if correct, when next pill is due ("Tomorrow 9 a.m.") or if not correct, issue a warning; caretakers can at any time upload (using NFC) a set of operational log data and verify that storage conditions and therapy were adhered to.

Figure 3:
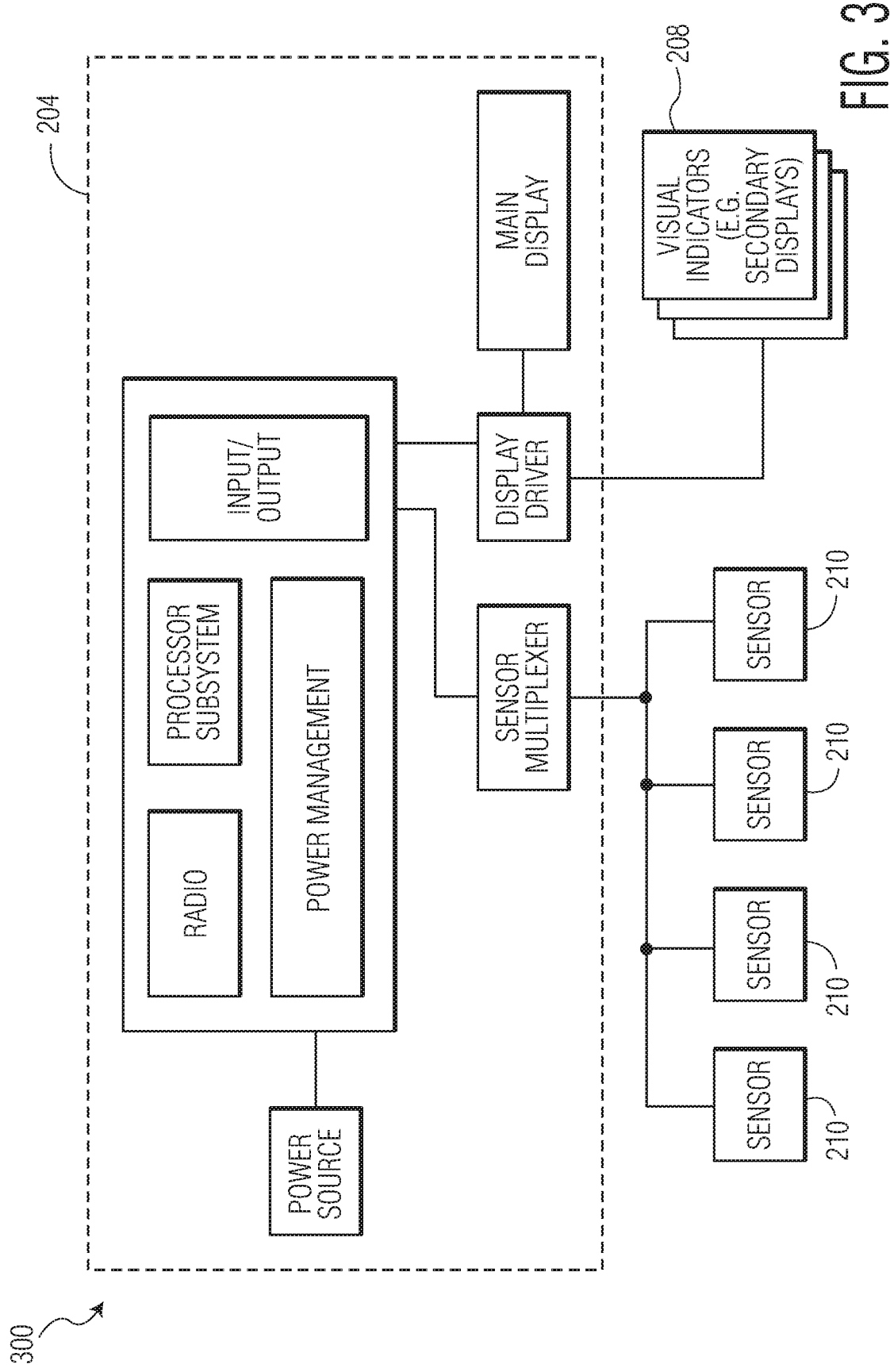
FIG. 3 shows an example functional schematic of the second example of the segmented platform

FIG. 3 shows an example functional schematic 300 of the second example of the segmented platform 202. The functional schematic 300 of the second segmented platform 202 includes the platform controller 204, the set of cells 206 (not shown), the set of visual indicators 208, and the set of detectors 210.

Figure 4A:
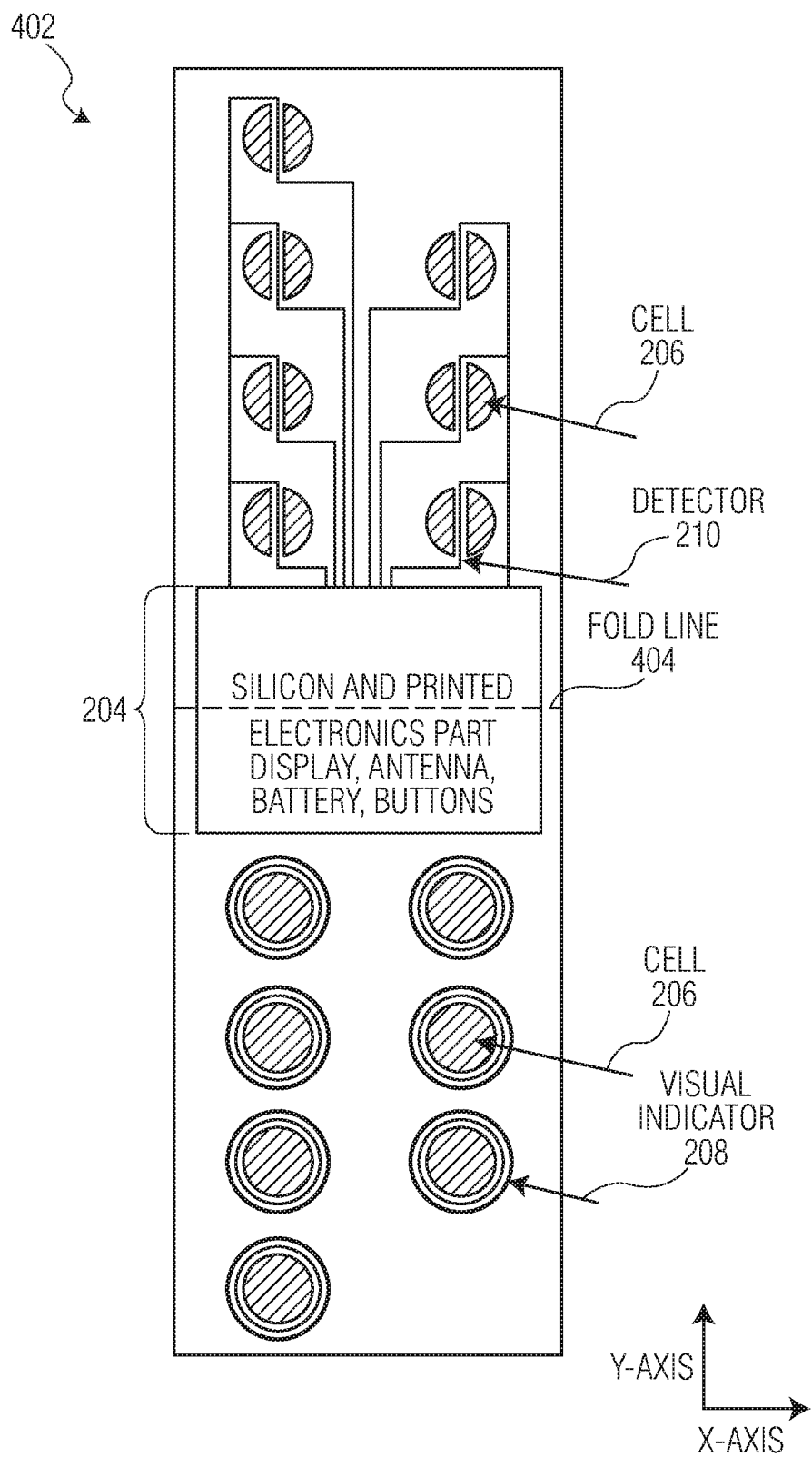
FIG. 4A is a third example of the segmented platform before folding.

FIG. 4A is a third example of the segmented platform 202 before folding 402. The segmented platform 202 before folding 402 shows the platform controller 204, the set of cells 206 (e.g. holes), the set of visual indicators 208 (e.g. pill indicator display), the set of detectors 210 (e.g. pill extraction sensor), and a fold line 404.

Figure 4B:
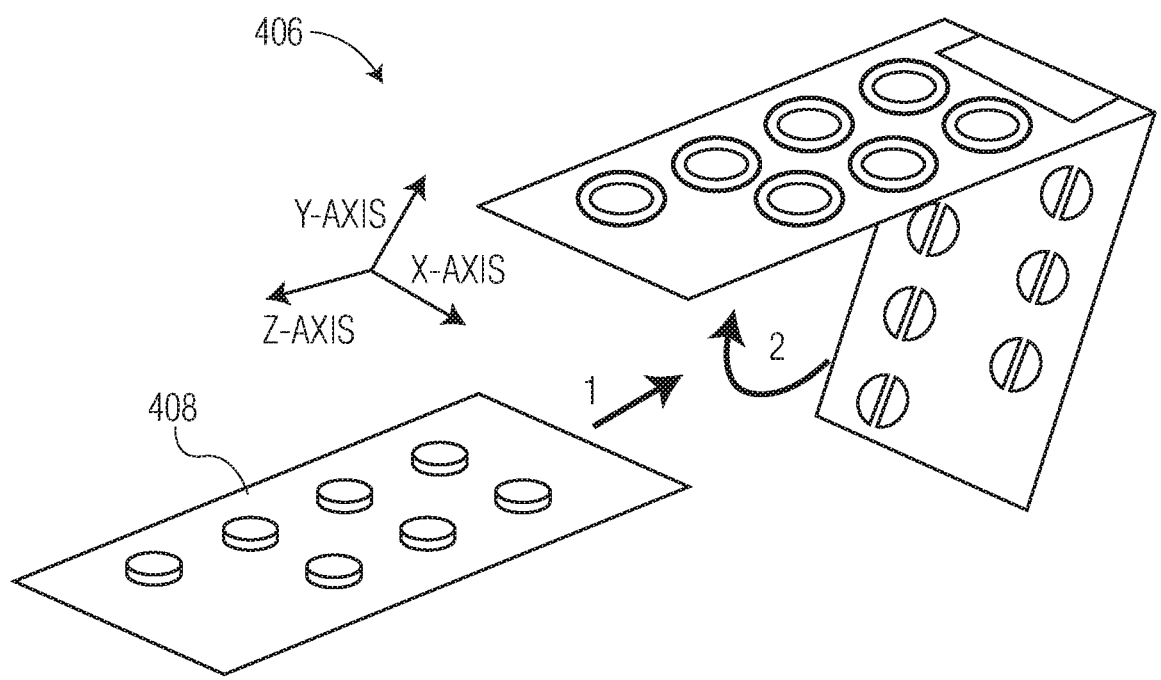
FIG. 4B is the third example of the segmented platform during folding.

FIG. 4B is the third example of the segmented platform 202 during folding 404. The segmented platform 202 during folding 406 shows a structure containing set of different items 408 (e.g. blister package) that is about to be inserted between the partially folded segmented platform 202.

Figure 4C:
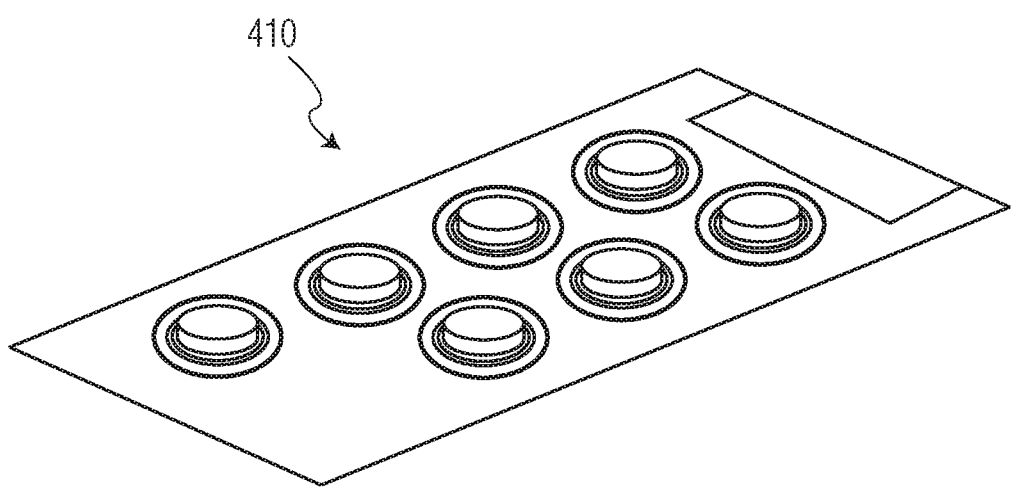
FIG. 4C is the third example of the segmented platform after folding.

FIG. 4C is the third example of the segmented platform 202 after folding 410. The segmented platform 202 after folding 410 shows the segmented platform 202 secured around the structure containing set of different items 408 with a coupling device (e.g. glue, adhesive, sticky surfaces, Velcro, latches, etc.).

Figure 5:
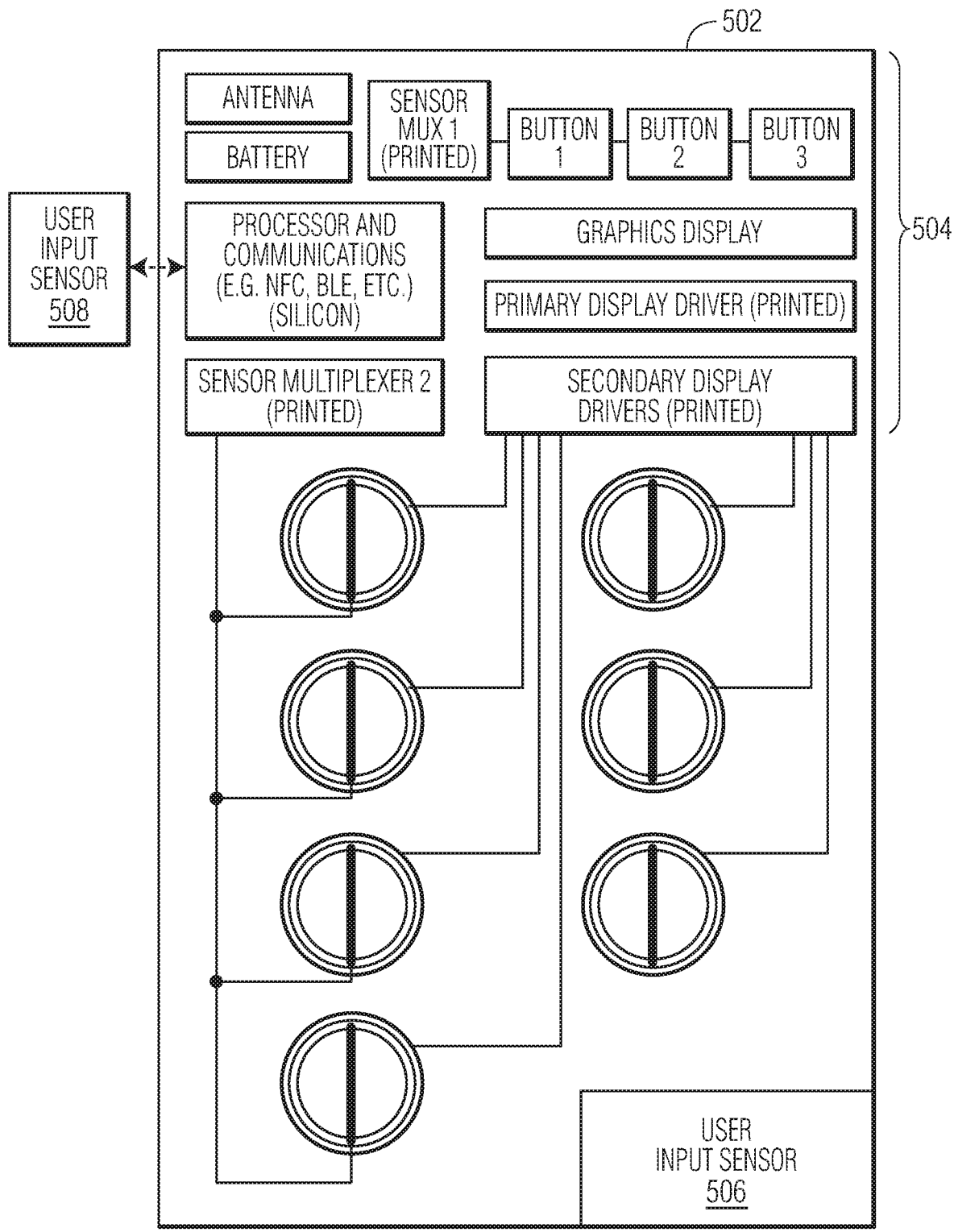
FIG. 5 is a fourth example of the segmented platform.

FIG. 5 is a fourth example 502 of the segmented platform 102. This fourth example 502 is substantially similar to the second example 202 discussed in FIG. 2, but with the following differences and/or enhancements. The segmented platform 502 includes a platform controller 504 (substantially similar to the platform controller 204), an integrated user input sensor 506 (e.g. biomarker sensor, temperature sensor, pH sensor, etc.), and an external user input sensor 508.

The user input sensors 502, 504 are configured to collect a set of user specific attributes. The user input sensors 502, 504 may be either embedded in a structure containing the set of different items, on the segmented platform 502, or remotely positioned somewhere else (e.g. remote blood pressure monitor). The user input sensors 502, 504 can be configured to communicate with the platform controller 504 either wirelessly or using wires.

The cell selector circuit 114 is configured to identify the selected item from the set of different items based on the set of user specific attributes received from the user input sensor. In one example embodiment, the cell selector circuit 114 is configured to identify the selected item from the set of different items based on a dynamic prescription received from a doctor.

In various embodiments of the segmented platform 502, the user specific attributes include at least one of: a user biomarker, blood pressure, glucose level, hormone level, virus or bacterial level, a problem identification level, a device upgrade level, a device repair level, or a professional skill level.

One example use case is as follows: the platform controller 504 is preloaded with or has access to a dynamic Doctor's prescription (e.g. a range of permissible medicine/pill dosages depending upon biomarker results); the internal user input sensor 502 and/or an external user input sensor 504 (e.g. biomarker sensor) measures a metabolite in a user's body fluid (e.g. a drop of a user's blood); a dosage selection algorithm receives the metabolite information and adjusts a timing of and/or calculates a dosage level according to the dynamic prescription; and the platform controller 504 then provides a visual indicator next to a specific cell containing a specific dosage required for the user to take.

Figure 6:
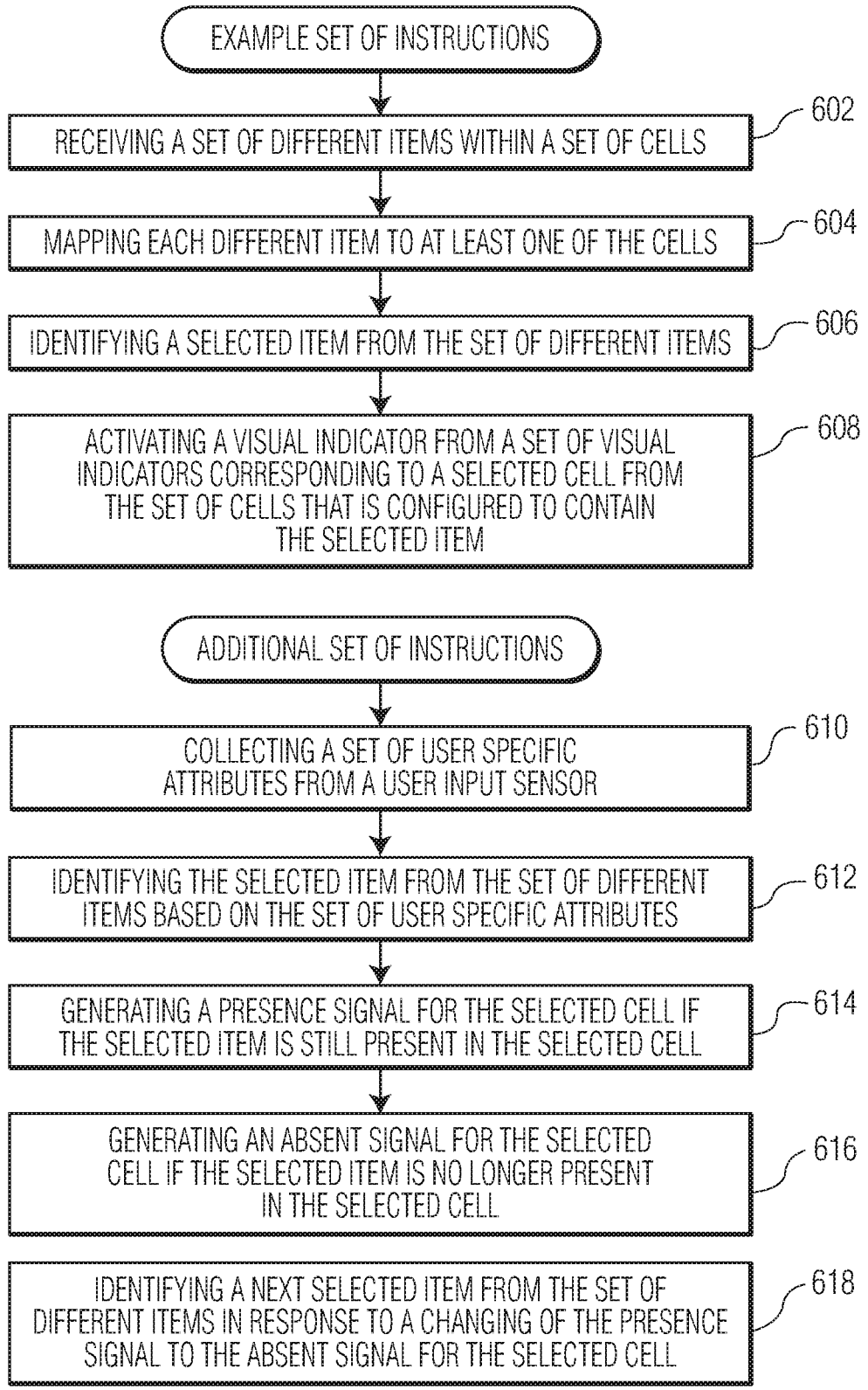
FIG. 6 is an example set of instructions for selecting cells within the segmented package.

FIG. 6 is an example set of instructions for selecting cells within the segmented platform (e.g. package). The order in which the instructions are discussed does not limit the order in which other example embodiments implement the instructions unless otherwise specifically stated. Additionally, in some embodiments the instructions are implemented concurrently.

A first example instruction set begins in 602, by receiving a set of different items within a set of cells. Next in 604, mapping each different item to at least one of the cells. Then in 606, identifying a selected item from the set of different items. And in 608, activating a visual indicator from a set of visual indicators corresponding to a selected cell from the set of cells that is configured to contain the selected item.

The instructions can be augmented or replaced with one or more of the following additional instructions, presented in no particular order: 610—collecting a set of user specific attributes from a user input sensor. 612—identifying the selected item from the set of different items based on the set of user specific attributes. 614—generating a presence signal for the selected cell if the selected item is still present in the selected cell. 616—generating an absent signal for the selected cell if the selected item is no longer present in the selected cell. 618—identifying a next selected item from the set of different items in response to a changing of the presence signal to the absent signal for the selected cell.

Figure 7:
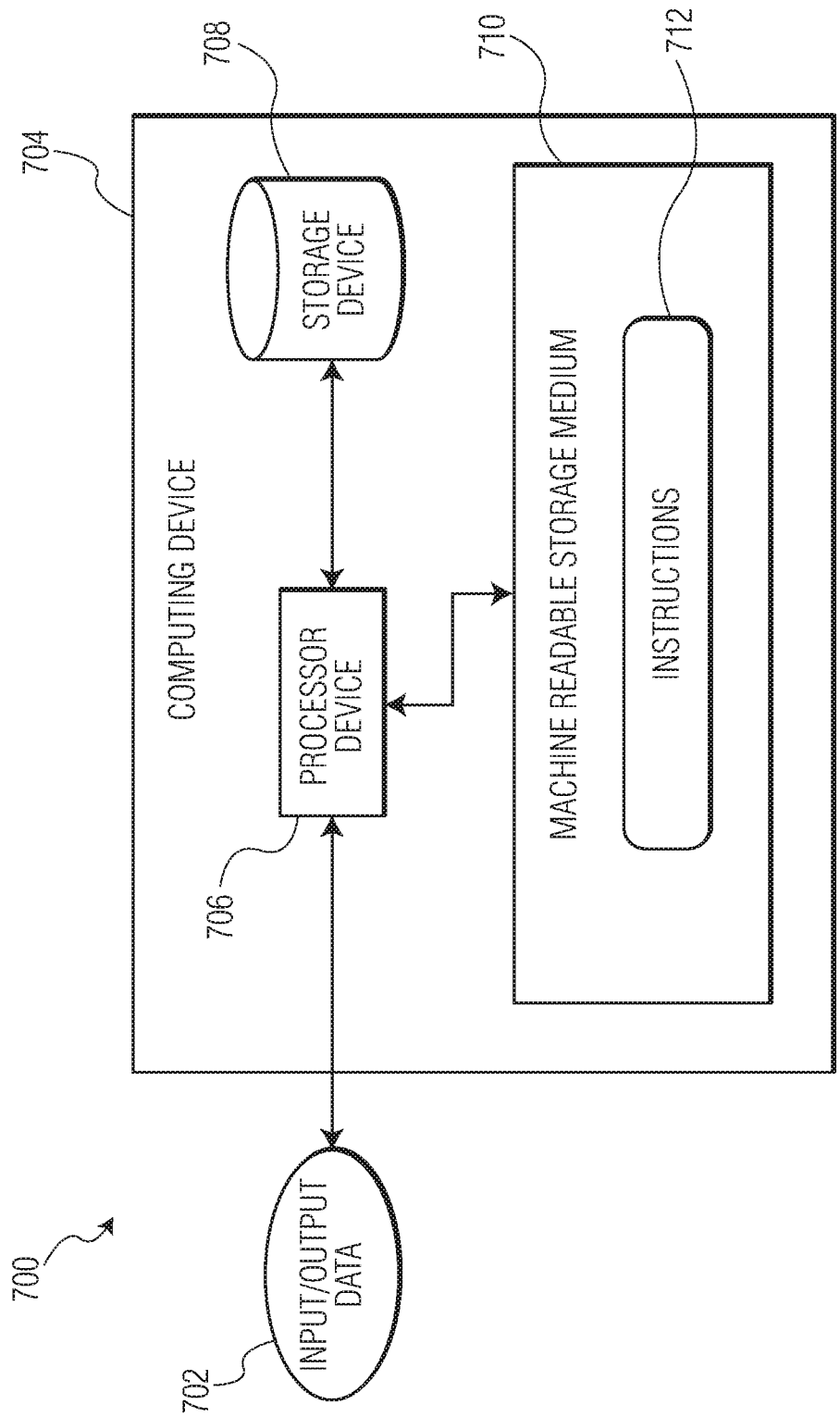
FIG. 7 is an example system for hosting the instructions of FIG. 6.

FIG. 7 is an example system 700 for hosting the instructions of FIG. 6. The system 700 shows an input/output data 702 interface with an electronic apparatus 704. The electronic apparatus 704 includes a processor 706, a storage device 708, and a non-transient machine-readable storage medium 710. The machine-readable storage medium 710 includes instructions 712 which control how the processor 706 receives input data 702 and transforms the input data into output data 702, using data within the storage device 708. Example instructions 712 stored in the machine-readable storage medium 710 are discussed elsewhere in this specification. The machine-readable storage medium in an alternate example embodiment is a non-transient computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and non-transient machine-readable storage medium using a bus and performs operations and tasks that implement one or more instructions stored in the machine-readable storage medium. The machine-readable storage medium in an alternate example embodiment is a computer-readable storage medium.

In some example embodiments the set of instructions described above are implemented as functional and software instructions. In other embodiments, the instructions can be implemented either using logic gates, application specific chips, firmware, as well as other hardware forms.

It will be readily understood that the components of the embodiments as generally described herein and illustrated in the appended figures could be arranged and designed in a wide variety of different configurations. Thus, the detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

What is claimed is:

1. A segmented platform, comprising:
   a set of cells configured to be optically projected over a folded structure containing a set of different items;
   a cell content circuit configured to map each different item of the set of different items to at least one cell of the set of cells;
   a set of visual indicators coupled to the set of cells, wherein the set of visual indicators pictorially represent a user quality score that increases based upon accurate use of the set of different items; and
   a cell selector circuit configured to identify a selected item from the set of different items and activate a visual indicator from the set of visual indicators corresponding to a selected cell from the set of cells.

2. The segmented platform of claim 1, wherein the folded structure is configured to receive a blister package.

3. The segmented platform of claim 1, wherein the set of different items differ by at least one of: a medicine dosage level, a quality level, an order of completion, an order of assembly, an order of repair, an order of food preparation, or a recipe.

4. The segmented platform of claim 1, wherein the set of different items include at least one of: a pill, a medicine, a disposable device, a repair kit item, an assembly kit item, a teaching kit item, a test kit item, a food, a nutrition level, an ingredient, or a chemical.

5. The segmented platform of claim 1, further comprising: a set of detectors configured to detect a presence of the set of different items.

6. The segmented platform of claim 5, further comprising: a cell status circuit coupled to the set of detectors and configured to generate a presence signal for the selected cell after the selected item is still present and generate an absent signal for the selected cell after the selected item is no longer present.

7. The segmented platform of claim 6, wherein the cell selector circuit is further configured to identify a next selected item from the set of different items in response to the cell status circuit changing the presence signal to the absent signal for the selected cell.

8. The segmented platform of claim 1, wherein multiple cells within the set of cells are configured to correspond to just one of the different items.

9. The segmented platform of claim 1, wherein the visual indicators include at least one of: a single visual indicator coupled to a single cell; a single visual indicator coupled to a set of cells; or a visual indicator pattern coupled to a set of cells.

10. The platform of claim 1, wherein the visual indicators pictorially represent a first color indicating the item to remove after the first defined period of time, the second color indicating the item to remove after the second defined period of time, and a third color indicating the item not to remove.

11. The segmented platform of claim 1, wherein the cell selector circuit is configured to identify the selected item from the set of different items based on at least one of: a medicine dosage level, a quality level, an order of completion, an order of assembly, an order of repair, an order of food preparation, a recipe, a chemical, or a type of material.

12. The segmented platform of claim 1, further comprising: a user input sensor configured to collect a set of user specific attributes, wherein the cell selector circuit is configured to identify the selected item from the set of different items based on the set of user specific attributes received from the user input sensor.

13. The segmented platform of claim 1, wherein the user specific attributes include at least one of: a user biomarker, blood pressure, glucose level, hormone level, virus or bacterial level, a problem identification level, a device upgrade level, a device repair level, or a professional skill level.

14. The segmented platform of claim 1, wherein the user input sensor is configured to be embedded in the folded structure containing the set of different items, and to be in communication with the segmented platform.

15. The segmented platform of claim 1, wherein the cell selector circuit is further configured to identify the selected item from the set of different items based on a dynamic prescription received from a doctor.

16. A method for selecting cells within a segmented package, comprising: receiving a set of different items in a folded structure, wherein a set of cells are configured to be optically projected over the folded structure containing the set of different items;
    mapping each different item of the set of different items to at least one cell of the set of cells;
    identifying a selected item from the set of different items; and
    activating a visual indicator from a set of visual indicators corresponding to a selected cell from the set of cells, wherein the set of visual indicators pictorially represent a user quality score that increases based upon accurate use of the set of different items.

17. The method of claim 16, further comprising:
    collecting a set of user specific attributes from a user input sensor; and
    identifying the selected item from the set of different items based on the set of user specific attributes.

18. The method of claim 16, further comprising:
    generating a presence signal for the selected cell after the selected item is still present;
    generating an absent signal for the selected cell after the selected item is no longer present; and
    identifying a next selected item from the set of different items in response to a changing of the presence signal to the absent signal for the selected cell.

* * * * *